(12) United States Patent
Nguyen (10) Patent No.: US 12,053,200 B2
(45) Date of Patent: Aug. 6, 2024

(54) POWERED INSTRUMENT

(71) Applicant: Medtronic Xomed, Inc., Jacksonville, FL (US)

(72) Inventor: Thoai Nguyen, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1132 days.

(21) Appl. No.: 16/741,152

(22) Filed: Jan. 13, 2020

(65) Prior Publication Data

US 2021/0212714 A1 Jul. 15, 2021

(51) Int. Cl.
*A61B 17/32* (2006.01)
*A61B 17/3203* (2006.01)
*A61B 17/00* (2006.01)
*A61B 17/16* (2006.01)

(52) U.S. Cl.
CPC .. *A61B 17/3203* (2013.01); *A61B 17/320016* (2013.01); *A61B 2017/00199* (2013.01); *A61B 2017/00398* (2013.01); *A61B 2017/00539* (2013.01); *A61B 2017/00544* (2013.01); *A61B 2017/00955* (2013.01); *A61B 17/1615* (2013.01); *A61B 2017/1651* (2013.01); *A61B 2017/320084* (2013.01); *A61B 2217/007* (2013.01)

(58) Field of Classification Search
CPC ........ A61B 17/3203; A61B 17/320016; A61B 17/1615; A61B 2017/00199; A61B 2017/00398; A61B 2017/00539; A61B 2017/00544; A61B 2017/00955; A61B 2017/1651; A61B 2217/007; A61B 2017/320084; A61B 2217/005; A61B 2218/001; A61B 2218/002; A61B 2218/007; A61F 9/00736

See application file for complete search history.

(56) References Cited

U.S. PATENT DOCUMENTS

| | | | | |
|---|---|---|---|---|
| 6,068,641 A | * | 5/2000 | Varsseveld | A61B 17/32002 606/170 |
| 9,622,767 B2 | * | 4/2017 | Stoddard | A61B 17/320092 |
| 2006/0241630 A1 | * | 10/2006 | Brunnett | A61B 17/1624 606/80 |
| 2011/0270293 A1 | * | 11/2011 | Malla | A61B 17/32002 606/180 |
| 2016/0106453 A1 | * | 4/2016 | Deeny | A61B 17/32002 606/170 |

(Continued)

FOREIGN PATENT DOCUMENTS

EP 2563247 A1 3/2013

OTHER PUBLICATIONS

International Search Report and Written Opinion regarding International Application No. PCT/US2021/012952, mailed Apr. 7, 2021.

(Continued)

*Primary Examiner* — Wade Miles
(74) *Attorney, Agent, or Firm* — Carter, DeLuca & Farrell LLP (57) ABSTRACT

Disclosed is a system to power a tool. The tool may be powered in a selected manner that may have irrigation and/or coolant provided therewith. The irrigation and cooling fluid may be provided at substantially at a working end and/or distal end of the instrument assembly.

18 Claims, 6 Drawing Sheets

(56) References Cited

U.S. PATENT DOCUMENTS

2017/0273698 A1* 9/2017 Mcguckin, Jr. ............................. A61B 17/320758

OTHER PUBLICATIONS

International Preliminary Report on Patentability regarding Patent Application No. PCT/US2021/012952, dated Jul. 28, 2022.
European Office Acton EP21704064.1 dated Jan. 1, 2024, 5pp.

* cited by examiner

POWERED INSTRUMENT

FIELD

The subject application relates to an instrument, and particularly to a powered instrument with a fluid passage.

BACKGROUND

This section provides background information related to the present disclosure which is not necessarily prior art.

A tool or tool tip may be operated in a selected manner to perform a procedure on a subject. The tool may include a selected bit or tip, such as a grinding burr, drilling bit, or other appropriate tip. The tip may be powered in a selected manner, such as through rotation from a motor. The motor may be an appropriate motor, such as an electric motor, hydraulic motor, or other appropriate motors to provide rotational force or torque to the instrument. The tool tip may then be rotated based upon the power provided by the motor to perform a procedure.

SUMMARY

This section provides a general summary of the disclosure, and is not a comprehensive disclosure of its full scope or all of its features.

Further areas of applicability will become apparent from the description provided herein. The description and specific examples in this summary are intended for purposes of illustration only and are not intended to limit the scope of the present disclosure.

Disclosed is an instrument assembly that is provided to allow a fluid (e.g. for irrigation and/or coolant) to pass through a cannula of an instrument assembly and directed onto and/or close to (e.g., immediately adjacent and/or in contact with) a distal tool tip. The instrument may include a powered handle, such as an electric, pneumatic, or hydraulic motor. The motor may rotate a portion of the tool tip to allow for a rotational speed and torque provided to a tool tip. The tool tip may be used to perform an action of work on a subject, such as adjacent to a structure thereof. The tool tip may include or be formed as a grinding burr, drilling bit, cutting burr, or other appropriate tip In various embodiments, an instrument assembly may include an electrically powered motor that provides torque and for power to a tool. The tool may include an elongated shaft and a distal tip. The distal tip may be used to perform work on a portion of the subject, such as remove hard materials in a subject, remove soft materials in a subject, bore portions in a subject, or the like. In various embodiments, the tool tip may be used to bore or remove bone, soft tissue, or the like in a subject. The subject may include any appropriate subject, such as a living subject (e.g., a human subject), or the like. In various embodiments, the tool may include a fluid path that allows for a selected material to be delivered or passed near a tip of the tool.

In various embodiments, for example, a motor may be provided in a hand piece. Connected to the hand piece may be an elongated cannulated portion, such as a cannulated shaft or instrument body. A tool may be connected to a portion of the motor to drive the tool. The tool may include an elongated shaft that extends through a cannulated portion of the instrument. Extending from the cannulated portion of the instrument may be a tool tip that is connected to the tool shaft. The tool shaft, therefore, may move the tool tip.

Provided relative to the cannulated portion of the instrument may be a fluid path. The fluid path may allow for delivery of the fluid material to an area relative to the tool tip. For example, the cannulated portion of the instrument may direct irrigation material toward the distal end of the tool and direct it internally toward a shaft of the tool. Thus, a procedure may be irrigated by directing an irrigation toward a distal end of the tool tip and/or immediately adjacent to and/or in contact with the tool tip rather than around a procedure area. The material may be a fluid (e.g. a liquid) that may flow toward the distal end.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
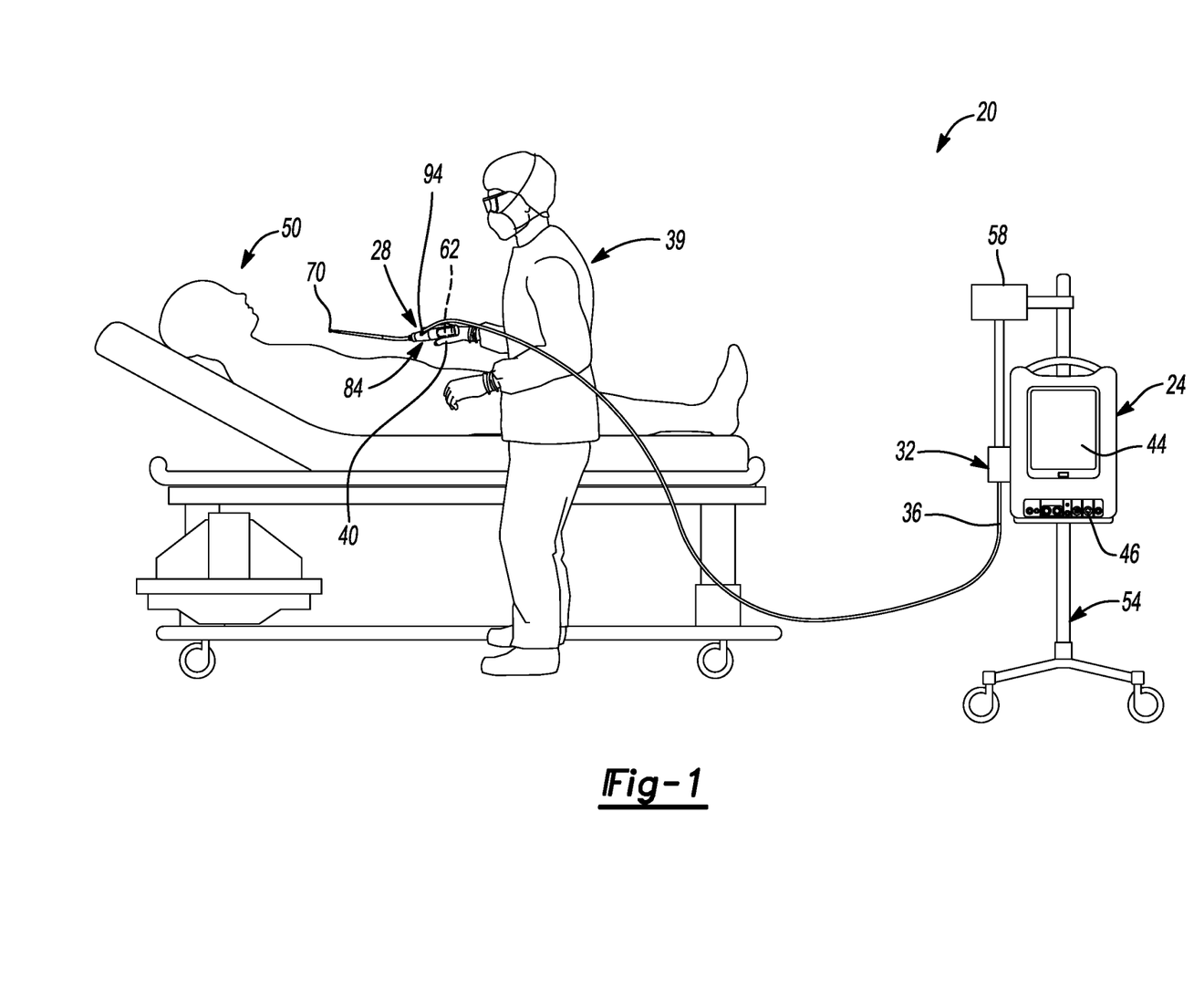
FIG. 1 is a schematic illustration of a procedure assembly.

With initial reference to FIG. 1, a procedure assembly 20 is illustrated. The procedure assembly 20 may include various portions, such as a control assembly or console 24 and an instrument assembly 28. The control console 24 may be any the appropriate control console such as the integrated power console (IPC®) system sold by Medtronic, Inc. having a place of business in Minneapolis, Minnesota. The control console 24 may include various portions for assisting in control of fluid flow or powering the instrument assembly 28. For example, the control console 24 may include one or more pumps 32 that may be used to provide or deliver a fluid, such as a liquid material, along a path or fluid path 36 (e.g. a tube) to the instrument assembly 28. The control console 24 may be operated by a user 39 that may use or hold the instrument assembly 28, such as with a hand or digit 40. The user 39 may operate the console 24 in any appropriate manner, such as using a touchscreen or screen portion 44. The control 24 may further include various control features, such as a remote that may be connected to the control console 24 such as through connections. The controls may include power to the motor, irrigation control 46, etc. The control console 24 may be provided in a selected procedure room, such as near a patient or subject 50 in an appropriate manner. In various embodiments, the control console 24 may be connected or provided on a movable stand or cart 54.

The control console 24 may be used to control the instrument assembly 28, or at least portions thereof, for a selected procedure. The pump assembly 32 may provide a fluid to the instrument assembly 28 from a fluid source 58 to the pump assembly 32 that is then pumped through the fluid path 36 to the instrument assembly 28. The control assembly 24, therefore, may be used to assist in controlling or providing selected features to the instrument assembly 28, such as a fluid supply, power supply (e.g., to power a motor 62 of the instrument assembly 28 to power, in a selected manner, a tool tip 70 of a tool portion 74 that may include a shaft 78). Accordingly, the instrument assembly 28 may include the tool portion assembly 74 and may be driven by and/or controlled by the control 24, as discussed further herein.

Figure 2:
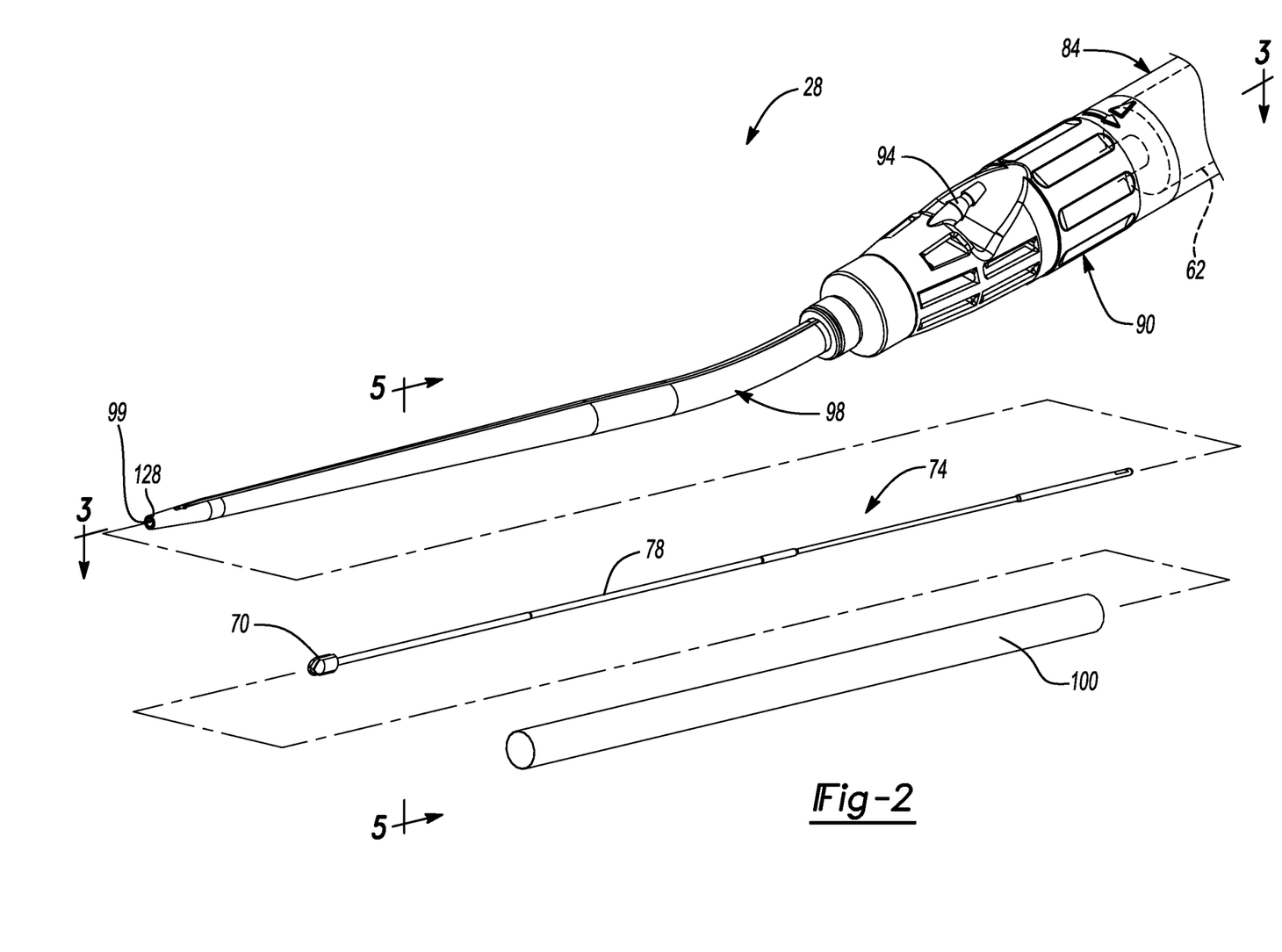
FIG. 2 is an exploded view of a working end of an instrument assembly.

With continued reference to FIG. 1 and additional reference to FIG. 2, the instrument assembly 28 includes the motor 62 in a housing or handle 84. The motor or handle housing 84 may be held by the hand 40, as discussed above. Further the motor 62 may be powered through connection with the control 24, as is generally understood in the art.

Connected to the handle housing 84 may be a collet or chuck assembly 90. The chuck assembly 90 can include various portions, such as those discussed further herein, including a fluid connection 94, which may be an irrigation connection that is connected with the tube 36. The instrument assembly 28 may further include an elongated tube or tool support member that may be an elongated tube 98. The elongated tube 98 may include or define a longitudinal bore there through, and thus, be a cannulated tube 98.

The cannulated tube 98 may be an internal tube that may be covered by a selected cover, such as an outer tube 100. The outer tube 100 may also define an elongated bore there through and thus, also be, an outer cannulated member 100. The outer cannulated portion 100 may cover a selected portion of the inner cannulated tube 98, as discussed further herein. The outer tube 100 may be concentric with the inner tube 98. Passing through the inner cannulated tube 98 and/or the outer cannulated tube 100 may be the tool 74. The tool 74 may extend through a portion of the chuck assembly 90 and have a motor connection portion or region that may have a selected feature to engage with the motor drive (e.g. flats). Thus, the tool 74 may be rotated due to the motor 62 when it is positioned within the inner tube 98.

The chuck assembly 90 may be used to hold and direct the tool 74. Various materials may be passed relative to the tool 74, such as an irrigation or cooling material, such as through the irrigation tube 36 that is connected to the irrigation connection 94. The irrigation material may allow for irrigating a portion near the tool tip 70, such as during the use and operation of the instrument assembly 28. Further, the irrigation material provided through the irrigation passage connection 94 may allow for cooling the tool instrument assembly 28 during operation thereof, such as operation and use of the tool 74.

Figure 3:
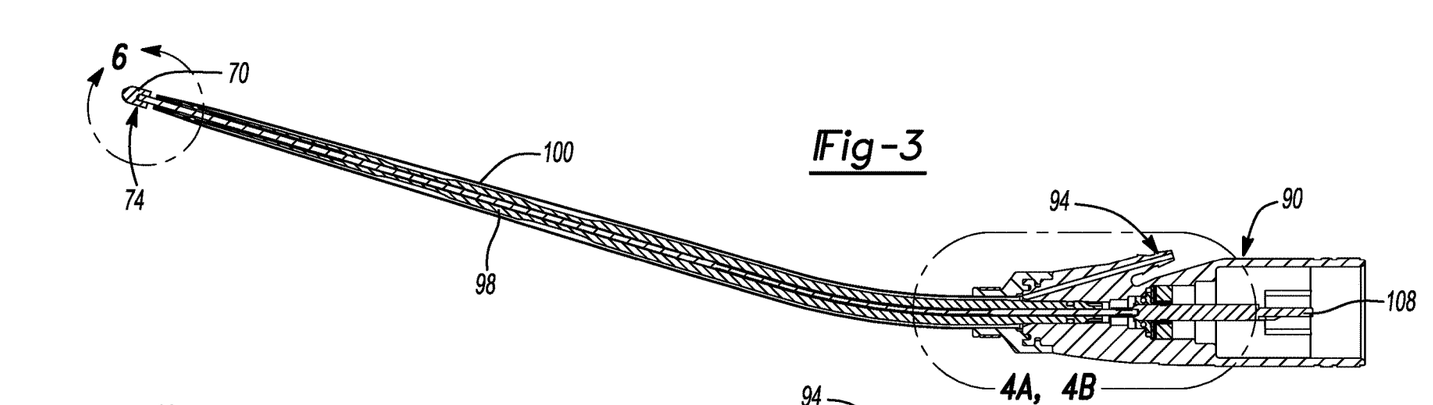
FIG. 3 is a cross-section view of the working end of the instrument assembly along line 3-3 of FIG. 2.
Figure 4A:
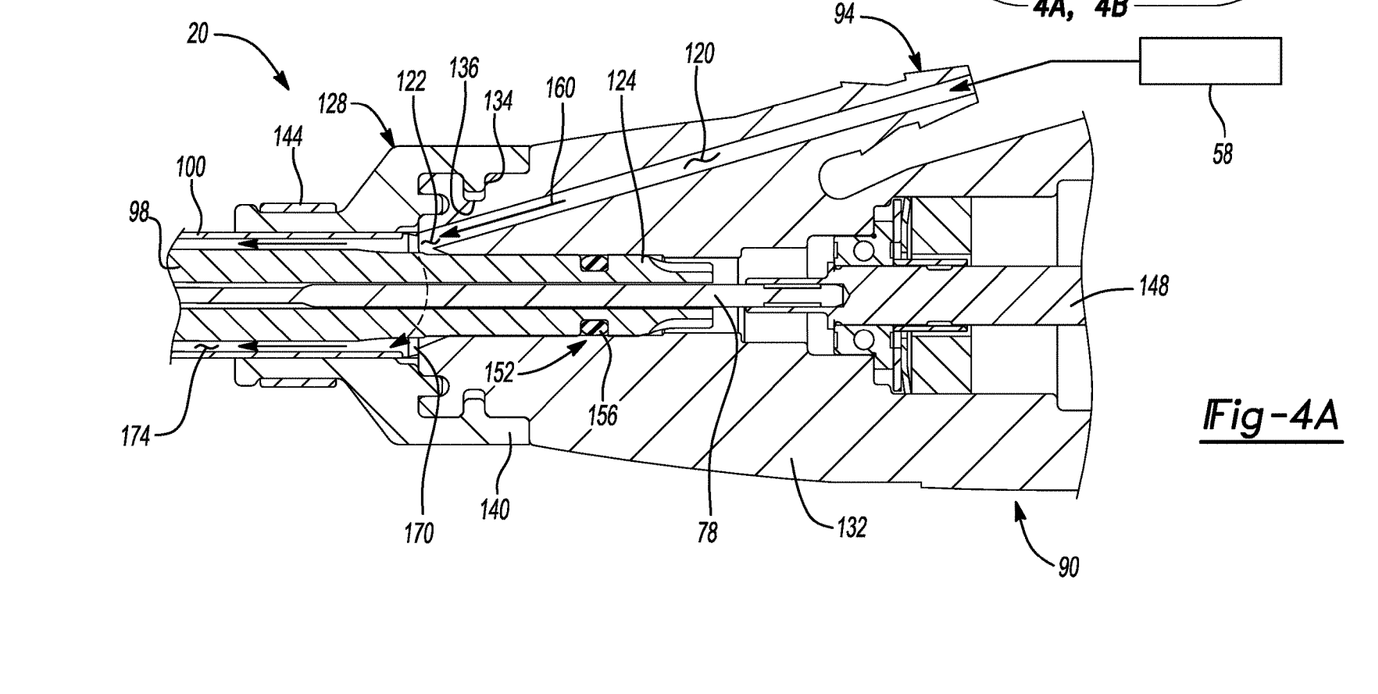
FIG. 4A is a cross-section view of a detail portion of the working end of the instrument assembly taken within circle 4A from FIG. 3.
Figures 4B, 5:
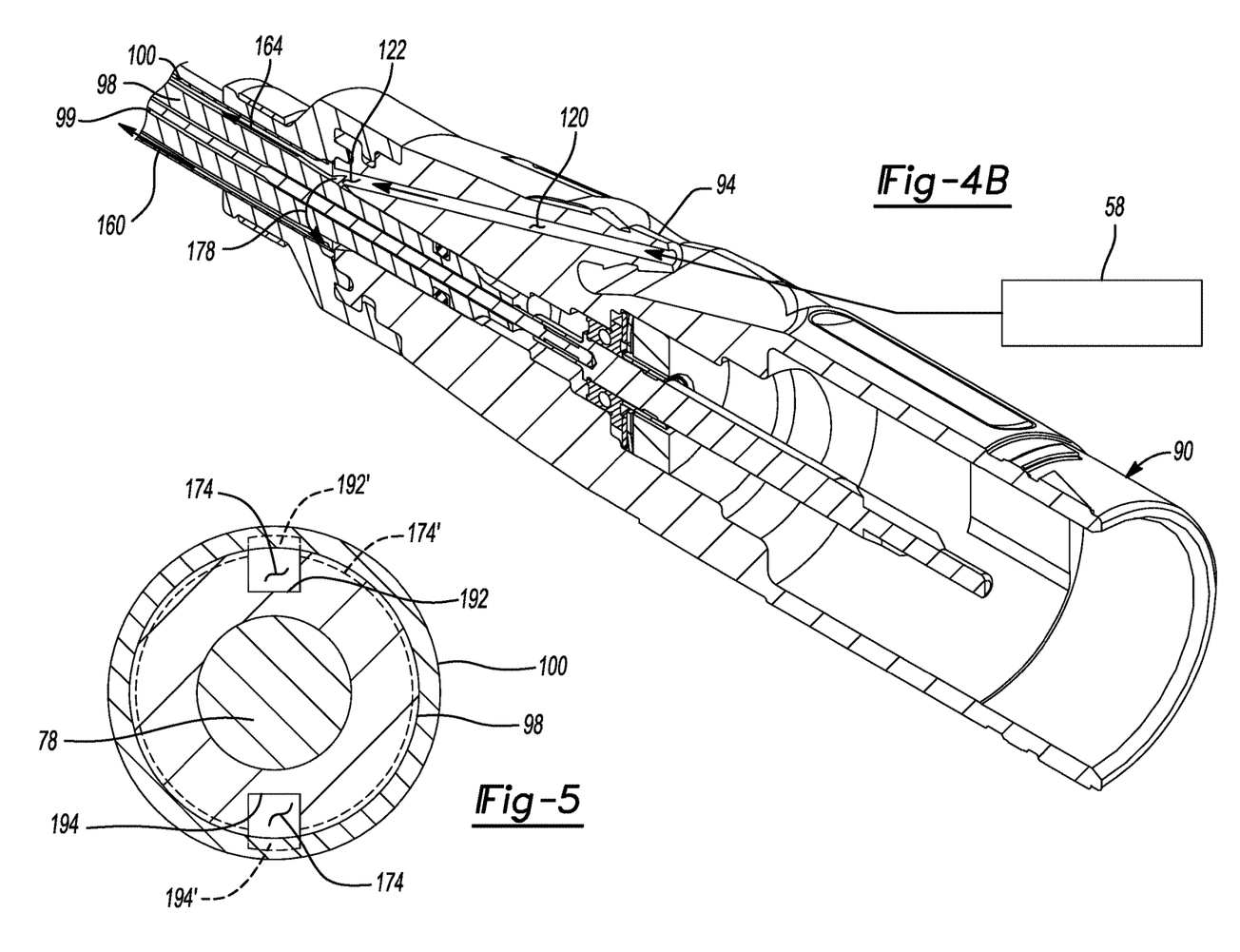
FIG. 4B is a detail cross-section perspective view of a detail portion of the working end of the instrument assembly taken within circle 4B from FIG. 3.
FIG. 5 is a cross-section view of a detail portion of the working end of the instrument assembly, along line 5-5 of FIG. 3.

With continued reference to FIGS. 2 and 3, and additional reference to FIG. 4A and FIG. 4B, the irrigation material (e.g., saline, distilled water, sterile water, combinations thereof or other such materials) may be passed through an initial or connection irrigation passage 120. The chuck assembly 90 may interconnect and engage the inner tube 98 at a proximal or first end 124. The inner tube 98 may further include a distal tip or end 128, as discussed further herein. At the proximal end 124 the inner tube 98 may be engaged within the chuck assembly 90 such as with an exterior connector or engagement member 128.

The exterior engagement or cap member 128 may be provided to engage a chuck body 132 in any appropriate manner, such as with threads, a snap or interference engagement, or the like. For example, one or more locking tabs 134 may engage a depression 136 in the chuck body 132. The projection 134 may engage the depression 136 by elastic rebound or deformation of an outer ring or finger 140. Also, a locking ring or member 144 may be provided to ensure an appropriate engagement with the inner tube 98. Regardless, the inner tube 98 may be held relative to the chuck body 132. As illustrated in FIG. 4A, the tool shaft 78 may engage a motor drive shaft 148. The engagement may be any appropriate engagement, such as a hex-drive or flat drive engagement. Thus, the tool 74 may be rotated within the inner tube 98.

The irrigation channel 120 may allow for irrigation material to be directed toward the inner tube 98. The inner tube 98 may include a depression or sealing region 152 near or at the proximal end 124. The sealing region 152 may include an O-ring 156. It is understood, however, that any appropriate sealing portion may be provided in the sealing region 152. Nevertheless, the sealing region 152 may maintain or eliminate passage of the irrigation material toward the motor drive shaft 148. The irrigation material, therefore, may be directed generally toward the distal end 128 of the inner tube 98, such as generally in the direction of arrow 160.

As illustrated in FIG. 4B, the outer tube 100 may be provided around (e.g. concentrically around) the inner tube 98, through which the tool 74 may pass. The outer tube 100 may circle or encompass the inner tube 98 in a substantially sealing manner. Further, the outer tube 100 may include a sealing or engagement flange or portion 170. The flange 170 may be engaged in the engagement or holding cap 128 relative to the chuck body 132. Thus, a substantially fluid tight seal may be formed between the outer tube 100 and the chuck body 132. The irrigation material will pass through the irrigation passage 120, such as generally along the direction of arrow 160, in an opening or passage area 174.

As illustrated in FIG. 4B, the irrigation material may also encircle or encompass the inner tube 98, such as in the general direction of the arrows 178. Thus, the irrigation material may pass through channels or passages, as discussed herein, between the outer tube 100, in the inner tube 98 in the general direction of arrows 160. With continued reference to FIG. 4A and FIG. 4B, and additional reference to FIG. 5 and returning reference to FIG. 2, the inner tube may include one or more channels, such as the first channel 192 and a second channel 194. The two channels may be generally opposed to one another, as illustrated in FIG. 5, or may be situated along any appropriate or selected portion of the inner shaft 98. Further, as discussed above, the tool shaft 78 may be positioned in an internal cannula or bore 99 of the inner shaft 98 for operation of the instrument assembly 28.

The fluid may pass through the channel 120 and be directed toward the inner tube 98. The fluid may initially gather in an area 122 at a proximal end of the outer tube 100. The area 122 may allow the fluid to encircle the inner tube 98. The fluid may then be provided to pass though the channels 192, 194 to the distal end near the tip 70. Thus, the fluid may enter through the passage 120 and initially gather or be directed in the area 122 and then enter the channels 192, 194.

With continued reference to FIG. 5, the inner tube 98 can cooperate with the outer tube 100 to form the fluid passages 174. The fluid passages 174 may be defined between the outer tube 100 and the inner tube 98, such as generally along the channels 192, 194. In various embodiments, the channels may be formed entirely by the inner tube 98. In various embodiments, the outer tube may form one or more channel 192', 194'. The channels, therefore, may be formed by a combination of the inner tube 98 and the outer tube 100, or by only one or the other.

It is understood that the outer tube 100 may also be provided to have a volume or space 174' between the outer tube 100 and the inner tube 98 along a length of the inner tube 98. The additional passage 174' may allow for a selected volume to fluid to flow to the distal end of the tube 98. The channels 192, 194, however, may also be provided as the only or singular passage along the majority of the length of the inner tube 98.

The outer tube 100 may be formed onto or provided onto the inner tube 98 in any appropriate manner. The outer tube 100 and the inner tube 98, therefore, may be used to form or provide the passage 174, 174'. The outer tube 100 may engage or encompasses and exterior of the inner tube 98. The passages 174, 174', therefore, may be provided on an exterior surface of the inner tube 98. As discussed herein, however, the fluid may be passed to an interior of the inner tube 98 at a selected location.

The outer tube 100 may be formed onto or provided onto the inner tube 98 in any appropriate manner. The inner tube 98 may be formed of a selected material, such as a metal or metal alloy or high melt temperature polymer or thermoset polymer. In various embodiments, the outer tube 100 may be formed of a selected material, such as a polymer material, that may be formed onto and/or placed on the inner tube 98. In various embodiments, the outer tube 100 may be provided as a substantially tubular member that is shrunk onto (e.g., heat shrunk) onto the inner tube 98. The outer tube 100 may be formed of a selected material, therefore, such as polyester that is able to be formed onto (such as by heat shrinking) the inner tube 98.

Alternatively, or in addition thereto, the outer tube 100 may be formed by dipping the inner tube 98 into a selected material, such as a polymer material. The dipped inner tube 98 may, therefore, have formed thereon a coating. The channels 192, 194 may have a removable or mask material placed therein that may be removed after dipping the inner tube 98 in the material. Thus, the channels 192, 194 may be vacated or opened prior to use of the assembly of the inner tube 98 and the outer tube 100.

The outer tube 100 may also be formed with selected tolerances and friction fit onto the inner tube 98. The outer tube 100 may also be adhered to the inner tube 98. Thus, the outer tube 100 may be formed onto or placed onto the inner tube 98 in any appropriate manner.

The heat shrink assembly, however, may not require or use a mask material within the channels 192, 194. Regardless, the outer tube 100 may be formed or provided onto the inner tube 98 to form an enclosed and substantially fluid tight channel or passage, along a portion or entire length of the inner tube 98.

Figure 6:
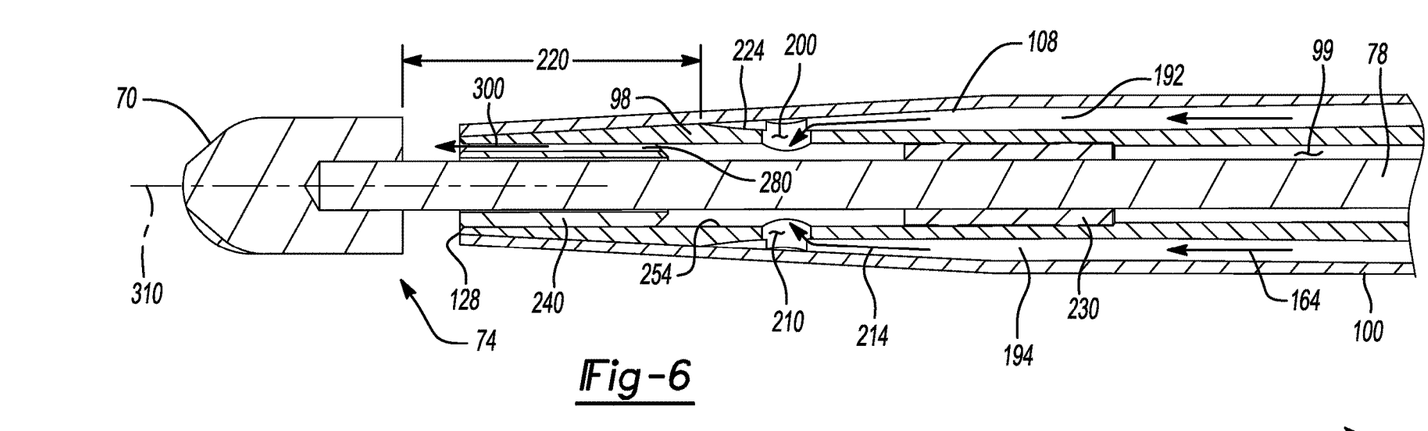
FIG. 6 is a cross-section view of a detail portion of the working end of the instrument assembly taken within circle 6 from FIG. 3.

With continued reference to FIGS. 1-5 and additional reference to FIGS. 6-9, near or at the distal end 128 of the inner tube is a passage or bore 200 extending from the channel 192 to the internal bore or cannula 99. In addition, however, as discussed above the inner tube 98 may also include the second channel 194. Accordingly, a second bore 210 may also be formed through the inner tube 98 from the second channel 194 to the internal cannula 99. Thus, as illustrated in FIG. 6, material that is moving in the direction of the arrow 164 may pass through the bores 200, 210 to pass into the internal cannula 99.

The fluid may flow generally in the direction of arrows 214 inward and toward a center or central axis of the internal tube 98 such as toward the tool shaft 78. The tool 74, as discussed above, can include the shaft 78 that extends along the inner tube 98 and terminates in a tool tip or head 70. The tool 74, therefore, may rotate as the fluid is moving in the direction of the arrows 214 and the fluid may pass near a portion of the tool 74, such as near the distal end 128 of the inner tube.

The outer tube 100 may assist in directing the fluid generally in the direction of the arrows 214 toward the tool 74. The outer tube 100 may seal relative to an outer surface of the inner tube 98, such as near a distal sealing portion or region 220 of the instrument assembly 28. As illustrated in FIG. 6, the inner tube 98 may include a ramp or angled region or wall 224 such that the outer tube 100 may engage and continuously seal to an outer wall of the inner tube 98 while allowing the channels 192, 194 to be open to allow fluids to pass along the channels 192, 194 generally in the direction of arrow 164. The sealing region 220 may therefore cause the fluid to move in the direction of the arrows 214 toward the internal cannula 99.

The instrument assembly 28 may further include a plurality of bushings, such as a proximal bushing 230 and a distal bushing 240. The bushings may assist in directing the fluid from the irrigation source after the fluid passes into the internal bore 99. The bushings 234, 240, as discussed herein, may assist in directing or moving the flow in an axial direction.

Figure 7:
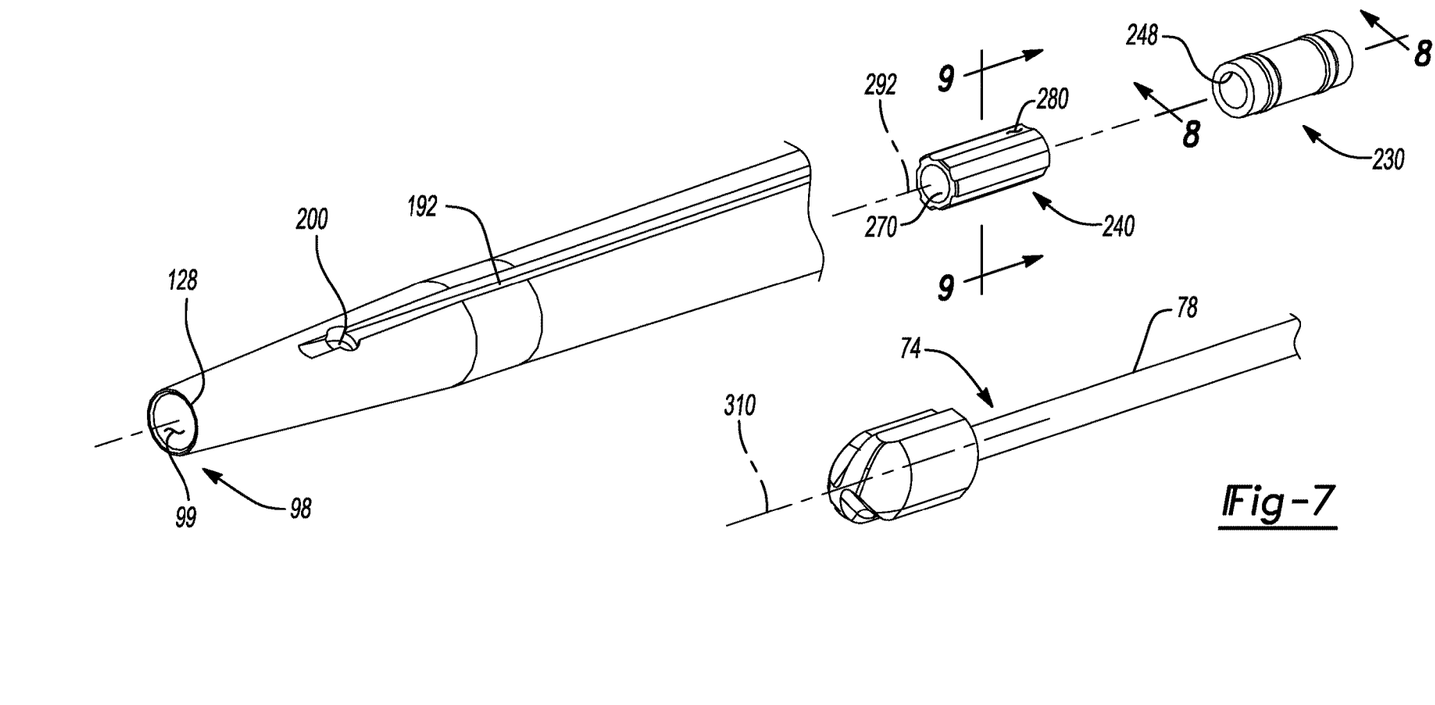
FIG. 7 is an exploded view of a working distal end of an instrument assembly.
Figure 8:
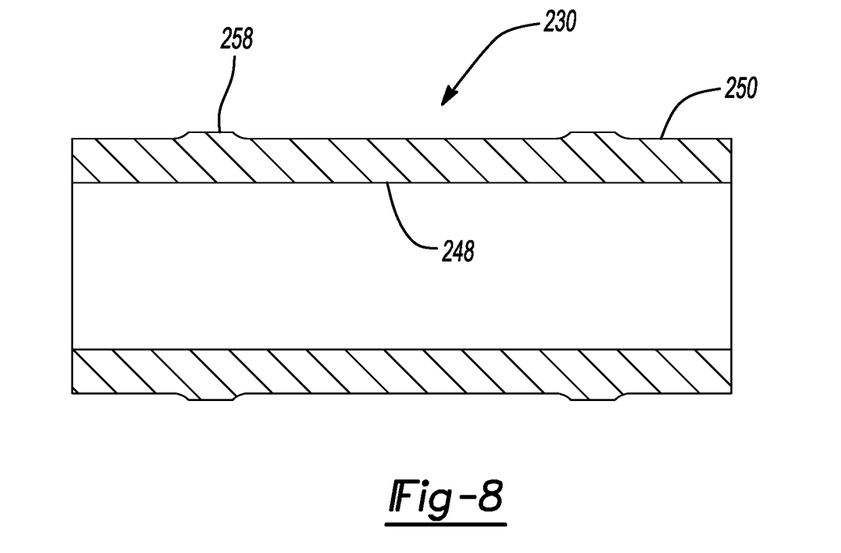
FIG. 8 is a cross-section view along line 8-8 of a proximal bushing of FIG. 7.
Figure 9:
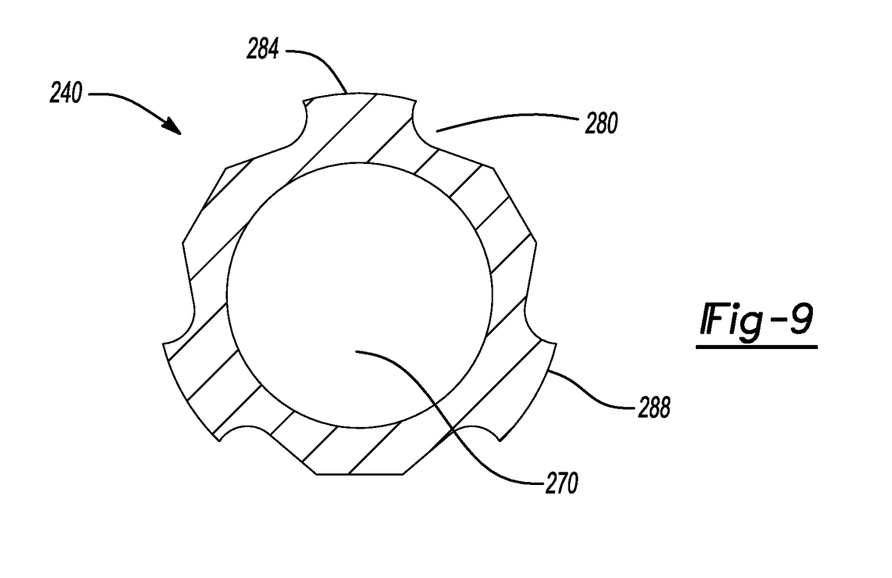
FIG. 9 is a cross-section view along line 9-9 of a distal bushing of FIG. 7.

With continued reference to FIG. 6 and additional reference to FIG. 7 and FIG. 8, the proximal bushing 230 may be formed of a selected material operable to perform as a bushing and/or seal. Exemplary materials include high performance thermoplastic materials such as PolyEtherEtherKetone (PEEK) or PolyArylEtherKetone (PAEK). The proximal bushing 230 may include a sealing surface such as an internal sealing surface 248 that is formed as a bore or passage through the proximal bushing 230. The tool shaft 78 may seal with the passage 248, but also rotate therein. The proximal bushing 230 may also include an external surface 250 that may seal with an internal surface 254 of the internal tube 98. In various embodiments the proximal bushing 230 may seal with the internal surface 254 with one or more raised ridges or projections 258 formed on the external surface 250 of the proximal bushing 230. It is understood, however, that the proximal bushing 230 may also have a substantially continuous external surface rather than the one or more ribs or raised portions 258 to seal with the internal surface 254 of the inner tube 98.

Accordingly, as illustrated in FIG. 6, the irrigation material moving generally in the direction of arrow 164 as it passes through the channels 192, 194 and then is directed into the internal cannula 99 generally in the direction of arrow 214 may be stopped from moving proximally in the direction of the motor shaft 148. Thus, the proximal bushing 230 may stop passage of fluid toward the proximal end 124 of the inner tube 98. Accordingly, at least two sealing portions may be provided to seal the motor or drive shaft 148 from the irrigation fluid. As discussed above the proximal sealing portion 152 and the proximal bushing 230 may eliminate or decrease irrigation fluid from moving proximally in the inner tube 98.

The instrument assembly 28 may further include the distal bushing 240. With continued reference to FIGS. 6 and 7 and additional reference to FIG. 9, the distal bushing 240 may provide a surface 270 to engage the shaft 78 of the tool 74. The bushing surface 270 may allow for a substantially smooth and low friction movement of the tool 74 when powered by the motor 62 via the motor drive 48, as discussed above. The distal bushing 240 may be formed in a similar or same manner and of similar or same materials as the proximal bushing 230. The distal bushing 240, however, may allow for directing fluid toward the tool tip 70 with directional channels or fluid guides 280. The channel or fluid guide 280 may be formed between one or more longitudinal or elongated projections, such as a first projection 284 and a second projection 288. The projections 284, 288 may extend along a longitudinal axis of the distal bushing 240, such as being formed substantially along the axis 292 defined through the distal bushing 240. The projections 284, 288 may generally engage the internal surface 254 of the inner tube 98. Thus, the distal bushing 240 may provide a bearing surface to hold the tool 74 during operation thereof but allow passage of the irrigation fluid passed the distal bushing 240 due to the fluid channels 280.

With continued reference to FIG. 6, therefore, irrigation fluid may generally pass through the fluid passages 280 generally in the direction of arrow 300 to exit out the end of the distal end 128 of the inner tube 98. The irrigation fluid generally moves in the direction of arrow 300 and may engage the working end of tip 70, such as due to a flow of the irrigation fluid in the direction of arrow 300. As illustrated in FIG. 6, the final path of the fluid before exiting may be substantially parallel with the axis 310. Thus, the path may be axial in the direction of arrow 300 and substantially radial along the arrow 214.

This allows the irrigation fluid 300 to be positioned substantially adjacent and/or at the working area due to passage of the irrigation fluid generally along the direction of the arrow 300 out the end and generally along and/or parallel to an axis 310 of the instrument 74. Thus, the irrigation material may be delivered substantially at the working area of the tool 74. In addition, the irrigation fluid may contact the distal head 70 at a selected rate to assist in the cooling and/or irrigation of the distal tip 70 of tool 74. In various embodiments, the fluid may exit the inner tube 98 only axially in the direction of arrow 300.

Accordingly, the instrument assembly 28, in the system 20, as discussed above, may be used to provide a fluid at the working tip 70 at a selected area. As discussed above the fluid may be a coolant and/or an irrigation fluid that may be directed along the inner tube 98 and substantially out the distal end 128 thereof. By passing the irrigation fluid out the distal end 128 of the inner tube 98, the irrigation fluid may be provided substantially at and/or immediately adjacent to the working tip 70 and/or working tip area of the instrument assembly 28. The fluid, therefore, may be directed more precisely and closely to a working area of the tip 70. Various parameters, therefore, may be achieved such as efficient irrigation for a procedure, cooling of the tip 70 and working surface, etc. The fluid may be used to clear the working area for viewing at the working tip 70.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument assembly, comprising:
    a fluid port;
    a fluid passage extending from the fluid port;
    a first elongated member defining an internal cannula;
    a second elongated member extending around the first elongated member;
    a channel formed between the first elongated member and the second elongated member and fluidly connected to the fluid passage;
    wherein a fluid is directed along the channel from the fluid port to near a distal end of the first elongated member, wherein the first elongated member includes an angled region disposed at a distal end thereof, the angled region angled in a radially outward direction to continuously seal against an inner periphery of the second elongated member and allowing the fluid to flow toward the internal cannula.

2. The assembly of claim 1, wherein the second elongated member is formed over the first elongated member.

3. The assembly of claim 2, wherein the second elongated member is a heat shrink material positioned over the first elongated member.

4. The assembly of claim 1, wherein the first elongated member has an exterior surface;
    wherein at least a portion of the channel is formed in the exterior surface;
    wherein the channel formed in the exterior surface is formed to extend toward a central longitudinal axis of the first elongated member from a first portion of the exterior surface;
    wherein the second elongated member contacts the first portion of the exterior surface and forms a fluid tight seal with the first portion of the exterior surface.

5. The assembly of claim 4,
    wherein the channel terminates prior to the distal end of the first elongated member; and
    wherein the second elongated member forms the fluid seal with the first portion of the exterior surface at the distal end of the first elongated member.

6. The assembly of claim 5, further comprising:
    a bore formed through a wall of the first elongated member from the channel to the internal cannula prior to the distal end; and
    wherein first elongated member forms a cannula and defines an internal bore;
    wherein the fluid moving through the channel is directed through the bore and into the internal cannula from the channel.

7. The assembly of claim 6, further comprising:
a proximal member positioned in the internal cannula; and
a distal member positioned in the internal cannula;
wherein the proximal member forms a fluid seal with an inner surface of the first elongated member.

8. The assembly of claim 7, wherein the distal member includes fluid passage channels to form fluid passage areas between an external surface of the distal member and the inner surface of the first elongated member.

9. The assembly of claim 1, further comprising:
a fluid source operable to supply the fluid to the fluid passage.

10. A method of providing a fluid to a distal end of an instrument assembly, comprising:
providing a fluid passage extending from a fluid port;
providing a first elongated member defining an internal cannula;
providing a second elongated member extending around the first elongated member; and
providing a channel between the first elongated member and the second elongated member;
wherein a fluid is directed into the channel from the fluid passage extending from the fluid port to a point near a distal end of the first elongated member, wherein the first elongated member includes an angled region disposed at a distal end thereof, the angled region angled in a radially outward direction to continuously seal against an inner periphery of the second elongated member and allowing fluid to flow toward the internal cannula.

11. The method of claim 10, further comprising:
providing a bore through a wall of the first elongated member from the channel to the internal cannula defined by the first elongated member,
the bore configured to direct the fluid into the internal cannula within the first elongated member.

12. The method of claim 11, further comprising:
sealing the fluid passage with the second elongated member.

13. The method of claim 12, further comprising:
heat shrinking the second elongated member to the first elongated member.

14. The method of claim 13, further comprising:
providing the second elongated member as a cannula.

15. The method of claim 10, further comprising:
supplying the fluid to the fluid port from a fluid source.

16. The method of claim 10, further comprising:
forming at least a portion of the channel in at least one of an exterior surface of the first elongated member or an interior surface of the second elongated member.

17. The method of claim 10, further comprising:
forming at least a portion of the channel in both of an exterior surface of the first elongated member and an interior surface of the second elongated member.

18. The method of claim 10, further comprising:
forming at least a portion of the channel in only one of an exterior surface of the first elongated member or an interior surface of the second elongated member.

* * * * *